United States Patent [19]

Dickson et al.

[11] 4,267,148
[45] May 12, 1981

[54] CORROSION MONITORING AND TESTING SYSTEM

[75] Inventors: Leon L. Dickson; Bart T. Ellison, both of Houston, Tex.

[73] Assignee: Shell Oil Company, Houston, Tex.

[21] Appl. No.: 101,969

[22] Filed: Dec. 10, 1979

[51] Int. Cl.³ ............................................. G01N 17/00
[52] U.S. Cl. .................................... 422/53; 23/230 C
[58] Field of Search ................. 422/53, 62; 23/230 C, 23/232 R; 116/208; 73/592, 432 SD, 86; 138/DIG. 6, 156, 157, 158

[56] References Cited

U.S. PATENT DOCUMENTS

| | | | |
|---|---|---|---|
| 1,905,974 | 4/1933 | Burke | 138/158 X |
| 3,093,223 | 6/1963 | Federico | 138/158 |
| 3,698,871 | 10/1972 | Brennan | 23/232 R |

OTHER PUBLICATIONS

Simons et al., "Corrosion and Components Studies on Systems Containing Fused NaOH", Battelle Mem. Inst., Report No. BMI-118, Jul. 30, 1956, pp. 2–11.

*Primary Examiner*—R. E. Serwin

[57] ABSTRACT

Method and apparatus for monitoring the corrosive effects of certain fluids by simulating the high temperature, high pressure, and flow conditions experienced in the production tubulars of oil and gas wells. A corrosion coupon constructed from an accurately machined tube is divided parallel to its axis and is held in place in a test chamber. A corrosive fluid is passed through the tube under simulated flow conditions at a controlled temperature and pressure. The tube is then dismantled for inspection so that loss of mass and the character of the loss from the divided sections due to corrosion may be determined.

12 Claims, 5 Drawing Figures

4,267,148

CORROSION MONITORING AND TESTING SYSTEM

BACKGROUND OF THE INVENTION

This invention relates to a corrosion monitoring system for testing the corrosive effects of certain fluids by simulating the high temperature, high pressure, and flow conditions experienced in the production tubulars of oil and gas wells. Various materials may be tested to determine their corrosion-resistant properties under controlled conditions and to determine the effects of various corrosion inhibitors.

In the production and handling of oil and gas, the tubulars and vessels which transport and store the petroleum products are often subject to highly corrosive fluid steams. Particularly severe corrosion may occur where the production contains high concentrations of carbon dioxide or hydrogen sulfide. Since corrosion rates may vary greatly as the temperatures, pressures, and flow conditions vary, it is important to test for corrosion under actual flow conditions. This may become difficult when the actual conditions are extreme, i.e., high temperatures, high pressures, and high velocity flow, and where the locations to be tested are inaccessible. For instance, in deep sour gas wells, actual well conditions may reach bottom hole pressures up to 20,000 psi and temperatures of 450° F., and depths at which the most severe corrosion may occur may be greater than 20,000 feet. In producing from these deep wells, the pressure-temperature conditions within the production tubing will decrease with decreasing depth according to the rate of production and cooling effects. Therefore, it is important in testing for corrosion to simulate the variable conditions which may exist along the length of the production tubing, while at the same time having the materials being tested readily available for inspection and analysis.

Because of the complex nature of the corrosion mechanism, corrosion rates may be best be determined by exposing the corrodable material to be tested to a corrosive environment in and out of the presence of corrosion inhibitor candidates. The most common techniques have been to rely on the weight loss after corrosion of a specimen of the material being tested. However, at inaccessible locations, these techniques have the disadvantage that the corrodable material may not be readily or economically retrieved for the weight loss determination. Other types of corrosion monitoring techniques have been developed to remedy this situation. Radioactive tracers have been developed so that corrosion determination may be accomplished at a position remote from the location of corrosion without recovering the test specimen which has been placed downhole. Some of these tracer techniques would only indicate the point at which a preselected degree of corrosion had taken place. However, these techniques have the earlier mentioned disadvantage that the tracer units had to be replenished periodically, resulting in time consuming and expensive operations where the location of corrosion determination was not readily accessible. Other tracer techniques, such as the radioactive sleeve technique described in U.S. Pat. No. 3,348,052 issued to Raifsnider et al have attempted to incorporate a minor amount of radioactive material in a specimen which gives a resulting composition having similar corrosion characteristics as the material being monitored. However, it was found that results were sometimes inaccurate due to uncertain calibration factors in calculating corrosion rates from the radioactive sleeves.

SUMMARY OF THE INVENTION

This invention is directed to a system for overcoming the shortcomings of the earlier techniques, especially where it is desired to test for corrosion at inaccessible locations such as downhole in oil and gas wells. However, this system works equally well where corrosion testing must be done for systems that are easily accessible, such as storage and process vessels. This system provides a number of corrosion coupons which can be tested under controlled conditions to simulate the production tubing environment of oil and gas wells, especially deep sour gas wells, as well as the environment of any process which undergoes corrosion. Each corrosion coupon is an accurately machined tube that has been divided parallel to its axis so that weight loss measurements and physical inspection can be accomplished without any loss of accuracy, such as those losses incurred by cutting the corrosion coupons for inspection. Various metals and various inhibitors can be evaluated simultaneously to determine their suitability for use as substitutes or replacement materials of various components which are present in the corrosive environment being simulated.

DESCRIPTION OF THE DRAWINGS

Advantages of the corrosion monitoring system of the invention will become apparent with reference to the detailed description in combination with the drawings, in which:

FIG. 3 represents the corrosion coupon in spatial relationship with two adapters and aligning bands.

DESCRIPTION OF PREFERRED EMBODIMENT

Figure 1:
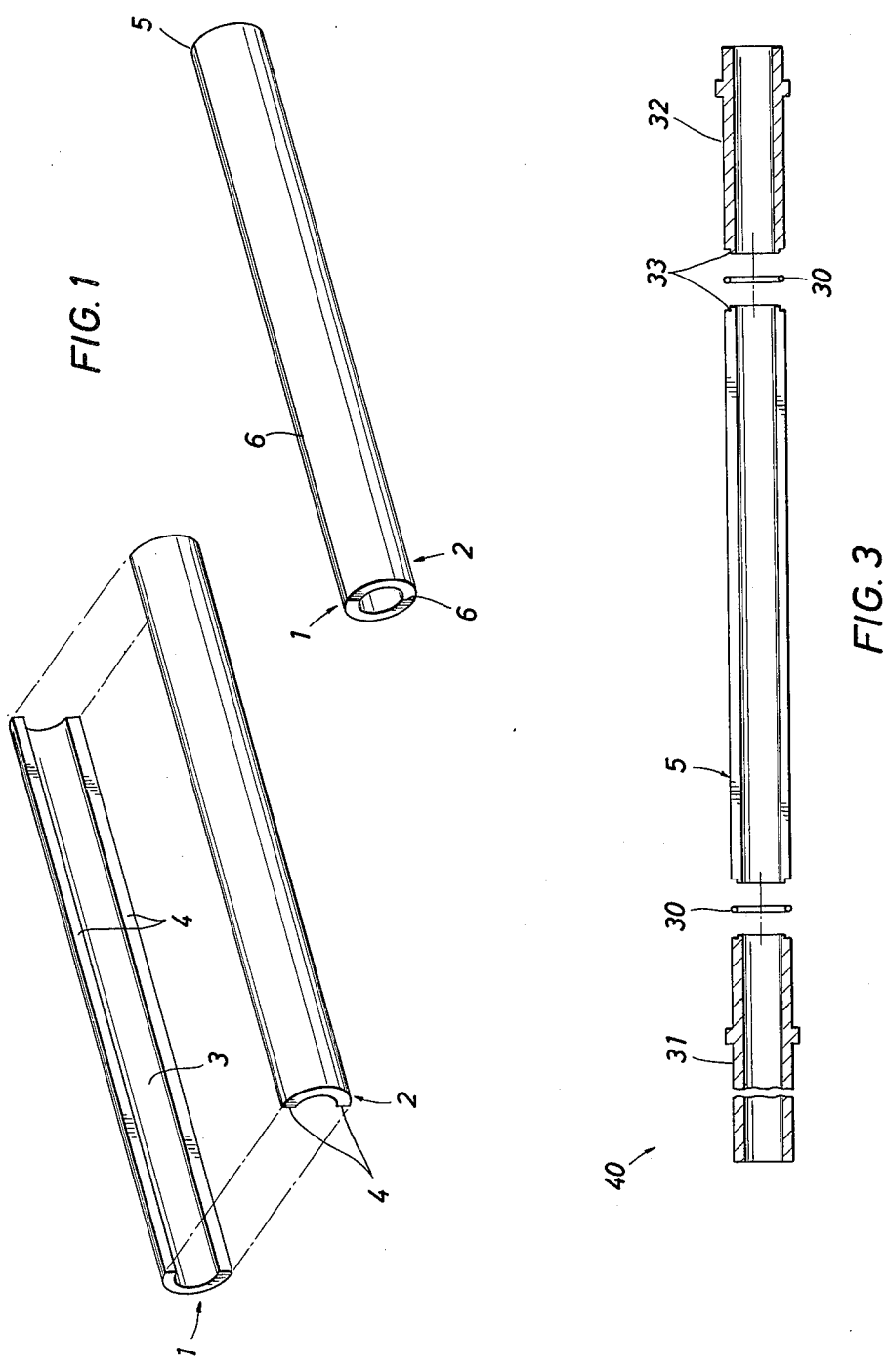
FIG. 1 represents a view of the component parts of the corrosion coupon.

Referring now to FIG. 1, there is shown a corrosion coupon 5 in the form of a sample tube divided along its axis into two parts, 1 and 2. The internal surface 3 of this test specimen is the active test piece, i.e., the surface which corrodes. The tubular geometry is especially desirable for purposes of the simulation system because well flow through production tubulars is thereby simulated. However, conventional tubular test specimens suffer from the disadvantage that some corrosion information is necessarily lost when the tubes must be split for examination. Therefore, the sample tubes of the invention are pre-split. Parts 1 and 2 of tube 5 are carefully fabricated so that the inside diameter is round and in tolerance. Edges 4 are carefully machined so that the tube may be externally sealed to retain the corrosive fluid within the corrosion coupon 5 when it is placed in service. The corrosion coupons may be constructed from tubing which is first gun-drilled to obtain a straight hole. The holes are reamed to tolerance and, using the center as a reference, the outside diameter is turned to size and ground to an exact outer diameter.

The tube is then cut into two parts such that at least one of the parts may be combined with one part from a second split tube to make one complete sample tube or corrosion coupon. The structure provides a coupon in the shape of a tube of exact dimensions with a finite crevice 6. Corrosive fluid contact is limited to the inner diameter and the crevice. The total mass of the reconstructed tube after division is substantially the same as before division, since any loss due to cutting is from the part that is discarded, rather than the part to be used as part of the coupon. Careful machining and close tolerance are necessary to insure that well flow characteristics are maintained within the sample tube. Excessively turbulent flow conditions caused by rough inner surfaces or irregularities would cause excessive corrosion rates, uncharacteristic of rates experienced in well tubulars.

Figure 2:
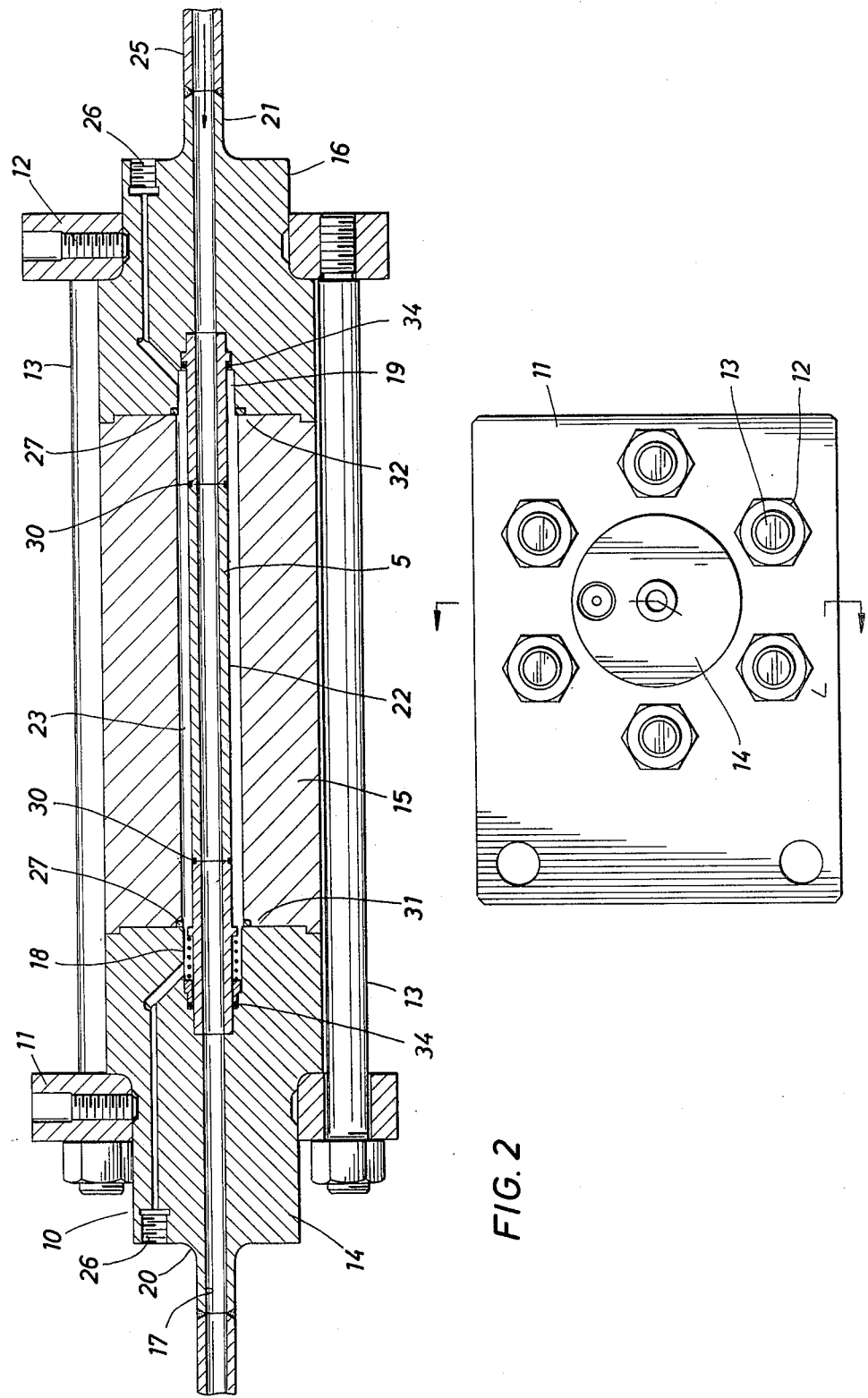
FIG. 2 represents a view of the corrosion coupon of the invention in its holder.

In FIG. 2, a holder for corrosion coupon 5 is shown whereby the parts of the sample tube are held in alignment so that there is no disturbance of the corrosive fluid as it flows through sample holder 10 and coupon 5. This alignment is accomplished as shown in FIG. 3 wherein corrosion coupon 5 is shown in spatial relationship with a first adapter 31 and a second adapter 32. The adjacent ends of the adapters and corrosion coupon are formed as illustrated at 33 so that bands 30 may be used to maintain the corrosion coupon in proper alignment with adapters 31 and 32 and to prevent the parts of corrosion coupon 5 from separating. Adapters 31 and 32 have been manufactured so that their inner diameters are substantially equal to the inner diameter of corrosion coupon 5. The complete structure 40 is then held in place as shown in FIG. 2 by flanges 11 and 12, which are held in place by bolts 13. Holder 10 as indicated in FIG. 2 is comprised of a first body portion 14, a main body 15, and a second body portion 16 which are held in an aligned position as aforementioned by flanges 11 and 12 and bolts 13. Main body 15 is used to enclose the sample tube in such a way that a finite tubulous volume surrounds the sample tube for purposes which will be explained. First body portion 14 is constructed so that it may be mounted adjacent main body 15. Body portion 14 has a centerbore 17 at least part of which has the same diameter as the inner diameter of corrosion coupon 5. In addition, body portion 14 may be provided with a receptacle 18 for mounting adapter 31 so that corrosion coupon 5 is mounted directly adjacent the adapter rather than adjacent body portion 14. Second body portion 16 is constructed to be mounted adjacent the opposite end of main body 15 from body portion 14. Body portion 16 serves a similar function as body portion 14, i.e., it has a bore therethrough for conducting the corrosive fluid through corrosion coupon 5 at least part of which is the same diameter as the inner diameter of the corrosion coupon. It may also be provided with a receptacle 19 for mounting adapter 32 therein. It is apparent that the function of main body 15, and body portions 14 and 16 is to provide a chamber which will contain sample tube 5 and which allows disassembling to remove the sample tubes for inspection. Thus, it would be possible to have only two body portions, rather than three, i.e., main body 15 and body portion 16 could be a single body portion, and a removable portion 14 would still allow disassembly and provide a fluid chamber. However, it would be more difficult to manufacture such a structure, and disassembly is enhanced with the three-part body of the preferred embodiment. As previously discussed, adapters 31 and 32 are provided to facilitate alignment of the parts of the sample tube before it is placed in sample holder 10. Body portions 14 and 16 may be provided with necked-down portions 20 and 21 respectively, so that external tubing may be readily interfaced with the sample holder, such as by screw-on mount or welding. The external tubing will then conduct the corrosive fluid toward and away from the sample holder. The tubulous volume mentioned above forms a fluid chamber 23 which facilitates sealing the parts of the sample tube to maintain the corrosive fluid within the corrosion coupon in the following way. A sleeve 22 may be provided which has an inner diameter only slightly greater than the outer diameter of the sample tube. This sleeve is sufficiently longer than the length of the sample tube so that it will overlap bands 30 and at least part of adapters 31 and 32, respectively. The sleeve should be made of any material which will not react in the presence of a corrosive fluid. It has been found useful to provide a sleeve made of Teflon (a registered trademark of E. I. DuPont de Nemours & Company for its tetrafluorethylene polymer plastic) for this purpose. In addition, it may be desirable to provide a heat-shrinkable sleeve 22 to obtain a tighter seal to the sample tube. In this way, adapters 31 and 32, corrosion coupon 5 and bands 30 may be placed together as shown in FIG. 3 with the heat-shrinkable tubing in place. Heat may be applied in any conventional manner in order to hold the parts in their respective positions. This complete structure (part 40 of FIG. 3 plus sleeve 22) may then be installed in sample holder 10. After connecting the sample holder to external tubing 25 and before conducting the corrosive fluid through the corrosion coupon, fluid chamber 23 is pressurized to ensure that sleeve 22 maintains a proper seal on corrosion coupon 5. For instance, the fluid chamber may be evacuated of air and hydraulically pressurized through ports 26 to a pressure of 23,000 psi if the flowing pressure of the corrosive fluid is 20,000 psi. The corrosive fluid will then reach the inner diameter of the corrosion coupon and crevices formed by the respective parts but will not be permitted to contact the outer surface. To ensure a proper seal, it has been found useful to install a second heat shrinkable sleeve 22' which extends slightly beyond each end of sleeve 22. Sleeve 22' may be made of viton rubber or some material which will not react in the presence of the pressurizing fluid which fills fluid chamber 23. The inner teflon sleeve is then held against the sample tube by the external loading of the pressurizing fluid acting against outer sleeve 22'. The viton sleeve forms the initial seal between the fluid chamber and the inner teflon sleeve to prevent the pressurizing fluid from reaching the inner sleeve. Silicone hydraulic fluid functions well as a pressurizing fluid in this instance. The crevice which is formed is of course desirable since this simulates a crack or threaded connection in the material of the corrosion coupon, and it is well known that a crack or threaded connection will exhibit more concentrated corrosion effects than a smooth surface. Thus, in addition to discovering the corrosion effects on the material of the corrosion coupon under controlled conditions, it is also possible to investigate the effects of corrosion on flaws or crevices simulating threaded connection in the material being tested.

When the corrosive fluid contains $H_2S$ it is possible to monitor the effectiveness of the seal formed by the coaction of the pressurized fluid chamber and the heat-shrinkable sleeve 22. Since silver will turn black in the presence of H₂S, the outer surface of the sample coupons may be silver plated. If the corrosive fluid containing H₂S should get past sleeve 22, it will be readily apparent when the corrosion coupon is dismantled for inspection.

To further ensure that fluid chamber 23 may be pressurized sufficiently to maintain the seal on sleeve 22 as previously discussed, "C" seals 27 may be provided at the junction of body portion 14 and main body 15, and body portion 16 and main body 15, respectively. In addition, "O" rings 34 may be utilized to provide proper seals between adapters 31 and 32 and their respective body portions.

Of course, the sample holders and adapters must be constructed from material which is resistant to the corrosive fluid which will be passed therethrough. It has been found that a Hastalloy C-276 alloy is especially useful for this purpose.

Figure 4:
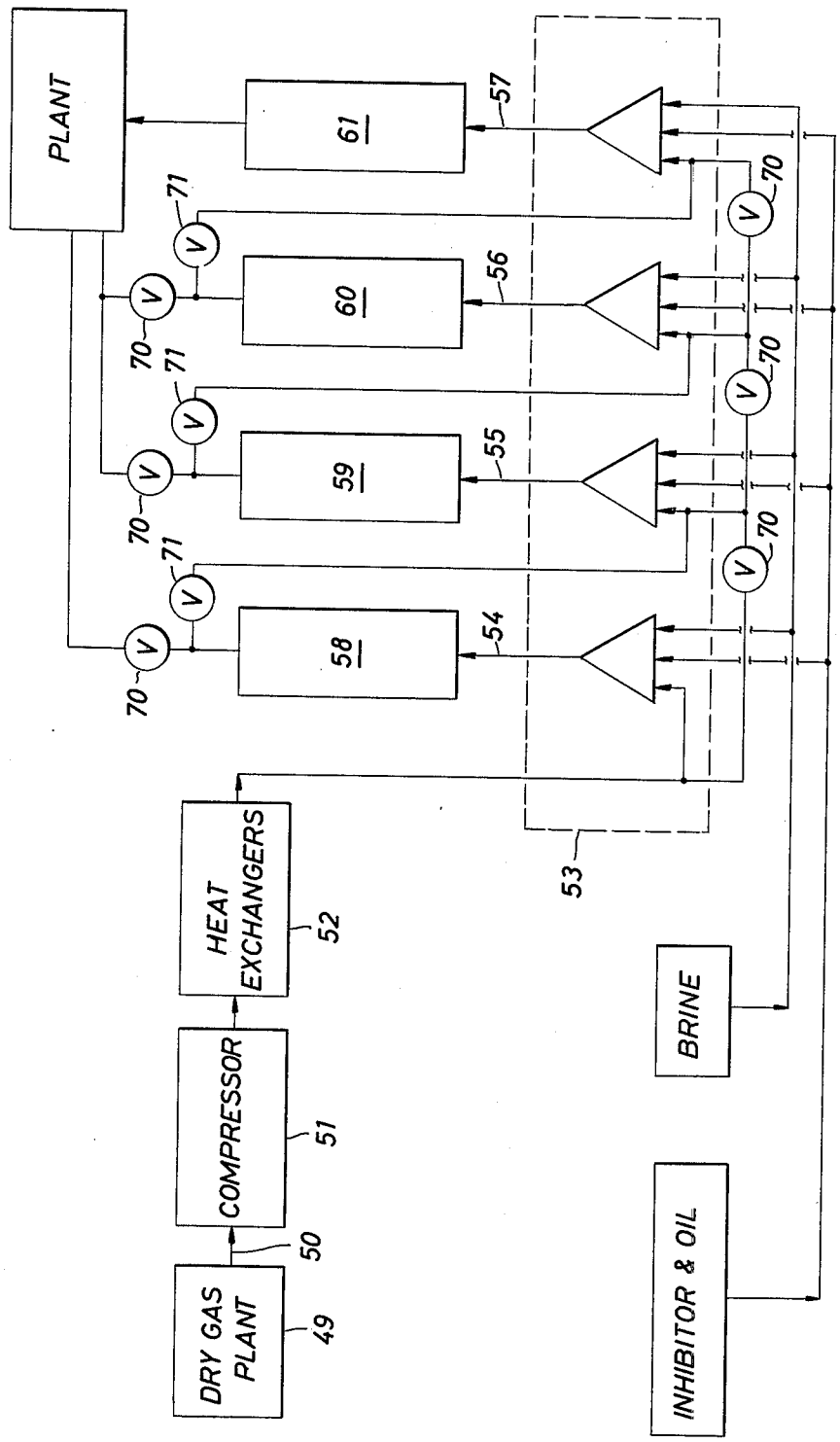
FIG. 4 represents a block diagram of the system for monitoring corrosion using the corrosion coupons of the invention.

Referring now to FIG. 4, the corrosion coupon and sample holder described above are shown in the corrosion monitoring system of the invention at points 58, 59, 60 and 61. The block diagram of FIG. 4 indicates that the corrosive fluid may be supplied by a plant where impurities have been removed. For instance, a typical stream from a gas plant may have a composition of 35% H₂S, 10% CO₂ and the balance of methane gas. At 50, sour gas from plant 49 is transported by pipeline to compressor 51, which may be a three-stage compressor for boosting the gas pressure to a desirable level. In this example, the gas is compressed to 20,000 psi before being sent to heat exchangers 52. At 52, the temperature of the gas is regulated to the desired value, which may be as high as 450° F. or higher. At 53, valve regulation is provided which may be automatic or manual at which point the sour gas is reconstituted by injecting varying amounts of impurities such as brine and inhibited oil (oil to which has been previously added various corrosion inhibitors). The gas samples entering at points 54, 55, 56 and 57 are therefore presented at flow rates, tempertures, pressures, and fluid compositions equivalent to those conditions existing at different positions in the well production tubing. These parameters may easily be changed to simulate relative positions in the production tubing of oil and gas wells. Sample holders 58, 59, 60 and 61 may contain corrosion coupons 5 of the same material, or different materials may be tested simultaneously. Candidate materials which are generally resistant to sour gas and which have been utilized are 4130 Steel (NACE sour gas specification), Hastalloy C-276, and MP35N(a multiphase alloy of 35% Ni, 35% Co, 20% Cr, and 10% Mo. It is also possible to vary the amounts, percentages, and types of the additives shown at 53 to determine the corrosive effects which are present with various inhibitors or varying amounts of the same inhibitor. Valves 70 and 71 of FIG. 5 perform the function of allowing the same or different combinations of corrosive fluid, brine, and inhibitors to be conveyed through sample tubes 58, 59, 60 and 61 in a parallel manner rather than the series manner required for the method described in FIG. 5, below. For parallel flow, valves 71 are closed and valves 70 are opened.

Figure 5:
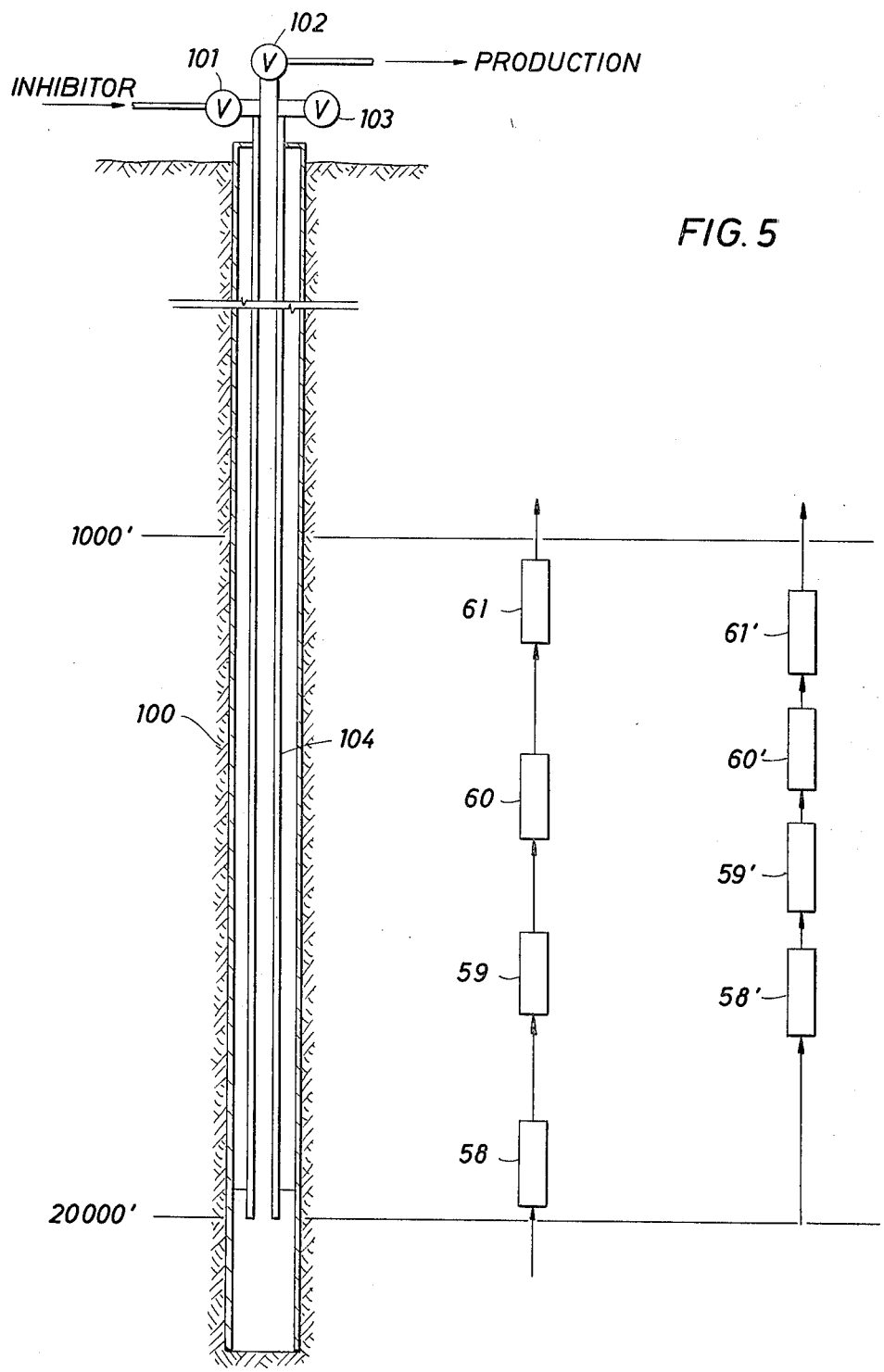
FIG. 5 represents one use of the corrosion monitoring system, i.e., monitoring corrosive effects at various depths in a producing well.

In FIG. 5, there is indicated an oil and/or gas well 100 which produces fluids with a corrosive content through production tubulars 104. Valves 101, 102 and 103 comprise what is commonly referred to in the oil and gas industry as a "christmas tree". Valve 101 regulates the amount of inhibitor which is pumped into the well to inhibit corrosion on tubulars 104. The depths of "1000 feet" and "20,000 feet" are illustrated merely to identify the utility of the system of the invention. Sample holders 58, 59, 60 and 61 are indicated in schematic form to the right of well 100 to show that, by varying the amounts, percentages, and types of additives combined at point 53 of FIG. 4 and by varying the pressure and temperature of the gas exiting the heat exchangers 52, conditions along production tubulars 104 may be simulated. For the series flow required, valves 71 are opened and valves 70 are closed. This is especially useful where it is necessary to design a unique production tubing string for a well which produces certain percentages and types of corrosive fluids as well as to select the optimum production tubulars for any type corrosion and the proper inhibitor to be used. As indicated by sample holders 58', 59', 60', and 61' by again varying the pressures, amounts, etc. at point 53 of FIG. 4 a different arrangement along production tubulars 104 may be simulated.

From the foregoing, it can be seen that a novel system of corrosion monitoring has been developed whereby a wide range of temperatures, pressures and flow conditions may be simulated to determine the effects of corrosion on a wide range of materials. A novel corrosion coupon is provided whereby exact flow conditions present in well tubulars may be duplicated and the corrosion coupons may be easily dismantled for internal inspection without loss of accuracy due to weight loss from cutting.

It will be understood that various modifications of this monitoring system may occur to those skilled in the art and it is intended that this invention be limited only by the scope of the appended claims.

What is claimed is:

1. Apparatus for monitoring the effects of certain corrosive fluids, comprising:

a sample tube divided along its axis into at least two parts, said parts having substantially the same mass as said tube before division, said tube having a finite inner diameter;

means for holding said sample tube having a fluid passageway therethrough substantially equal to said sample tube inner diameter, said means sealingly engaging said sample tube at each end such that fluid flow through said holding means and said sample tube occurs without restriction; said means for holding said sample tube comprising a main body for enclosing said sample tube having an opening therethrough of a larger cross-section than the cross-section of said sample tube, said opening comprising a fluid chamber;

a first body portion for joining said main body at one end in alignment with said opening having a passageway therethrough at least part of which has the same diameter as the inner diameter of said sample tube, said first body portion providing for connecting to corrosive fluid flow;

a second body portion for joining said main body at its other end in alignment with said opening having a passageway therethrough at least part of which has the same diameter as the inner diameter of said sample tube, said second body portion providing for connecting to corrosive fluid flow; and, means for clamping said first body portion, said main body, and said second body portion in a longitudinal orientation for fixedly supporting said sample tube within said fluid chamber, whereby said holding means may be dismantled and the sample tube parts examined for effects of corrosion after the corrosive fluid has been passed through said sample tube.

2. Apparatus according to claim 1, including:

a first adapting member engaged with said first body portion having a passageway therethrough substantially the same diameter as the inner diameter of said sample tube, said passageway being in alignment with the passageway of said first body portion for joining said sample tube at its first end;

a second adapting member engaged with said second body portion having a passageway therethrough substantially the same diameter as the inner diameter of said sample tube, said passageway being in alignment with the passageway of said first body portion, for joining said sample tube at its second end; and, sealing means placed concentric with said first and said second adapting members for sealing the spaces between said adapting members and said respective body portions.

3. Apparatus according to claim 1, including means for maintaining said sample tube in proper alignment with said first and said second body portions and for preventing said parts of said sample tube from separating.

4. Apparatus according to claim 1, including evacuating and pressurizing means for hydraulically pressuring and evacuating said fluid chamber such that no corrosive fluid is allowed to escape from said apparatus except through the passageways of one of said body portions.

5. Apparatus according to claim 4, wherein said fluid chamber is pressurized with a fluid which will not react adversely upon contacting the corrosive fluid.

6. Apparatus according to claim 4, wherein said fluid chamber is pressurized with silicone hydraulic fluid.

7. Corrosion monitoring system for monitoring the effects of corrosive fluids, comprising:

a source of corrosive fluid;

temperature regulating means for varying the temperature of said corrosive fluid;

means for combining said corrosive fluid with impurities to simulate well streams;

at least one sample tube divided along its axis into at least two parts;

said parts having substantially the same mass as said tube before division, said tube having a finite diameter;

means for transporting said combined corrosive fluid through said sample tube inner diameter; and, means for holding said sample tube having a fluid passageway therethrough substantially equal to said sample tube inner diameter for transporting said corrosive fluid therethrough, said means sealingly engaging said sample tube at each end such that fluid flow through said holding means and said sample tube occurs without restriction.

8. Apparatus according to claim 7 including means for regulating the pressure of said corrosive fluid.

9. Apparatus according to claim 7, wherein said combining means comprises a number of regulating valves for combining varying amounts of said impurities with said corrosive fluid resulting in different combinations, and for transporting said different combinations to different sample tubes, respectively.

10. Apparatus according to claim 9, including at least four sample tubes, each sample tube monitoring the corrosive effects of a different combination of impurities and corrosive fluids.

11. Apparatus according to claim 7, wherein said combining means combines amounts of corrosion inhibitors and oil with said corrosive fluid so that corrosion inhibiting effects on said sample tube may be monitored.

12. Apparatus according to claim 7, wherein said combining means and said temperature regulating means are used to simulate flow conditions at different depths in a producing well.

* * * * *